United States Patent [19]

Noguchi et al.

[11] 4,018,817
[45] Apr. 19, 1977

[54] 6-HALO-5-CYCLOHEXYLINDAN-1-CARBOHYDROXAMIC ACID

[75] Inventors: Shunsaku Noguchi; Yoshiaki Araki, both of Osaka; Masayuki Imanishi, Hyogo; Kiyohisa Kawai, Kyoto, all of Japan

[73] Assignee: Takeda Chemical Industries, Ltd., Osaka, Japan

[22] Filed: Nov. 30, 1973

[21] Appl. No.: 420,459

[30] Foreign Application Priority Data

Dec. 7, 1972 Japan ............... 47-122874

[52] U.S. Cl. ............... 260/500.5 H; 260/247.5 R; 260/268 C; 260/293.62; 260/556 B; 260/558 R; 260/558 H; 260/558 P; 260/247.7 R; 424/250; 424/267; 424/321; 424/324; 424/248.57

[51] Int. Cl.² ............... C07C 83/08; A61K 31/165

[58] Field of Search ............... 260/558 R, 500.5 H

[56] References Cited

UNITED STATES PATENTS

| | | | |
|---|---|---|---|
| 2,798,888 | 7/1957 | Ueberwasser et al. | 260/570.8 R |
| 3,312,730 | 4/1967 | Winter et al. | 260/558 R X |
| 3,505,404 | 4/1970 | Petersen et al. | 260/558 R X |
| 3,532,752 | 10/1970 | Shen | 260/558 R X |
| 3,565,943 | 2/1971 | Juby et al. | 260/469 |
| 3,622,623 | 11/1971 | Shen et al. | 260/558 R X |
| 3,644,479 | 2/1972 | Juby et al. | 260/558 R X |
| 3,763,229 | 10/1973 | Noguchi et al. | 260/558 R X |
| 3,923,866 | 12/1975 | Sawa et al. | 260/558 A X |
| 3,953,500 | 4/1976 | Noguchi et al. | 260/558 R X |

*Primary Examiner*—Daniel E. Wyman
*Assistant Examiner*—Thomas A. Waltz
*Attorney, Agent, or Firm*—Wenderoth, Lind & Ponack

[57] ABSTRACT

A novel indan-1-carboxamide derivative of the formula

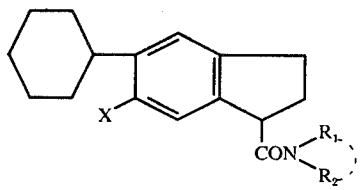

wherein X represents hydrogen or a halogen; $R_1$ represents hydrogen, a lower alkyl group which may be substituted with hydroxyl group or represents phenyl group; and $R_2$ represents a lower alkyl group which may be substituted with hydroxyl, phenyl or an N,N-dilower-alkylamino group, or represents hydroxyl group, an amino group which may be substituted with a mono- or di-lower alkyl group, phenyl group or with a halophenyl group, or represents a phenyl group which may be substituted with a halogen or a mono- or di-lower alkyl group, a lower alkoxyl group or with sulfamoyl group; or $R_1$ and $R_2$, together with the adjacent nitrogen atom, form a piperidino group, a morpholino group or a piperazino group which may be substituted with a lower alkyl group on the 4-positioned nitrogen atom, which compounds are useful as medicines, for example, analgesic, anti-inflammatory, anti-pyretic or anti-rheumatic agents.

2 Claims, No Drawings

6-HALO-5-CYCLOHEXYLINDAN-1-CARBOHYDROXAMIC ACID

This invention relates to novel indan-1-carboxamide derivatives useful as medicines, for example analgesic, anti-inflammatory, antipyretic or anti-rheumatic agents.

More particularly, the present invention relates to indan-1-carboxamide derivatives of the formula:

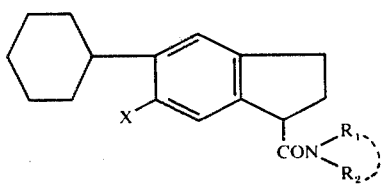
(I)

wherein X represents hydrogen or a halogen; $R_1$ represents hydrogen, a lower alkyl group which may be substituted with hydroxyl group or represents phenyl group; and $R_2$ represents a lower alkyl group which may be substituted with hydroxyl, phenyl or an N,N-diloweralkylamino group, or represents hydroxyl group, an amino group which may be substituted with a mono- or di-lower alkyl group, phenyl group or with a halophenyl group, or represents a phenyl group which may be substituted with a halogen or a mono- or di-lower alkyl group, a lower alkoxyl group or with sulfamoyl group; or $R_1$ and $R_2$, together with the adjacent nitrogen atom, form a piperidino group, a morpholino group or a piperazino group which may be substituted with a lower alkyl group on the 4-positioned nitrogen atom.

Referring to the above definitions, the term "halogen" means fluorine, chlorine, bromine and iodine. The term "lower alkyl" includes those having preferably 1 to 6 carbon atoms (e.g. methyl, ethyl, n-propyl, i-propyl, n-butyl, t-butyl, i-butyl, pentyls and hexyls). Among those, alkyl groups having 1 to 3 carbon atoms are more preferable. The term "lower alkoxyl group" includes those having preferably 1 to 3 carbon atoms (e.g. methoxy, ethoxy, propoxy and i-propoxy). It should be understood that, throughout the present specification and the claims each of the lower alkyl groups represented by the term "di-lower alkyl" may be the same as or different from each other.

The principal object of the present invention is to provide the compound (I).

Another object of this invention is to provide a process for producing the compound (I).

Further object is to provide a pharmaceutically useful compound (I), especially useful in treating fevers, rheumatism, inflammatory diseases and pains.

Other objects will be apparent from the following description and claims.

The compound (I) may be prepared by reacting a compound of the formula

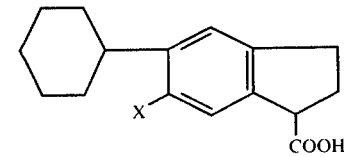
(II)

(wherein X has the meaning defined above) or a reactive derivative thereof at its carboxyl group with a compound of the formula $$NH \begin{matrix} R_1 \\ R_2 \end{matrix}$$ (III)

(wherein $R_1$ and $R_2$ have the meanings defined above).

The reactive derivatives of the compound (II) at the carboxyl group may for example be esters, acid halides (e.g. chlorides and bromides), acid azides, acid amides, acid anhydrides and ketonitriles of the compound (II). The esters of the compound (II) may for example be alkyl(e.g. methyl, ethyl, propyl), aryl (e.g. phenyl) or aralkyl (e.g. benzyl and phenethyl) esters. The acid anhydrides of the compound (II) may for example be those formed by condensation with dehydration of two molecules of a compound (II), mixed anhydrides fromed condensation with dehydration of a compound (II) and an organic carboxylic acid (e.g. formic acid acetic acid) or an inorganic acid (e.g. sulfuric acid, boric acid and silicic acid) and carbonic acid monoalkyl esters (e.g. monoethyl carbonate).

In the method of the present invention, a compound (II) or a reactive derivative thereof at its carboxyl group is allowed to react with a compound (III).

The compound (III) may be employed in the form of its acid salts such as hydrochloride, sulfate, hydrobromide, nitrate, p-toluenesulfonate or acetate. The compound (III) may be employed in an amount generally ranging from about 1 to about 20 moles, preferably about 1 to about 10 moles per mole of the compound (II) or its reactive derivatives.

This reaction may be carried out in the presence or absence of a solvent. The solvent may for example be water, alcohols (e.g. methanol and ethanol), ethers (e.g. diethyl ether, dipropyl ether, tetrahydrofuran and dioxane), hydrocarbons (e.g. benzene, toluene, hexane and petroleum ether), halogenated hydrocarbons (e.g. chloroform, carbon tetrachloride and methylene chloride), nitriles (e.g. acetonitrile), ketones (e.g. acetone and methyl ethyl ketone), amides (e.g. dimethylformamide and dimethylacetamide), dimethyl sulfoxide, amines (e.g. trimethylamine, triethylamine and pyridine). The compound (III) per se can serve as solvent as well.

The reaction can be usually conducted at a temperature ranging from about −10° C to about 50° C or it may sometimes proceed around the boiling point of solvent used. There may be a case where the present reaction proceeds advantageously in the presence of a dehydrating agent when the starting compound (II) is employed in the form of free carboxylic acid or in the presence of a base when the compound (II) is employed in the form of acid halides. The dehydrating agents may for example be cyclohexylcarbodiimide and triphenylphosphine-bromotrichloromethane. The bases may for example be alkali metal hydroxides (e.g.

sodium hydroxide and potassium hydroxide), alkaline earth metal hydroxides (e.g. calcium hydroxide and barium hydroxide), alcoholates (e.g. sodium methoxide and sodium ethoxide), alkali metal carbonates (e.g. sodium carbonate and potassium carbonate) and amines (e.g. trimethylamine, triethylamine and pyridine). These bases may be used generally in an amount of about 1 to about 25 moles per mole of the compound (II) or its reactive derivatives.

The compound (I) can be easily collected from the reaction mixture by per se conventional means, for instance, by evaporating the solvent under reduced pressure. The compound (I) may form acid salts when $R_2$ is a lower alkyl group which is substituted with an N,N-di-lower-alkylamino group, or $R_1$ and $R_2$, together with the adjacent nitrogen atom, form a piperazino group which may be substituted with a lower alkyl group on the 4-positioned nitrogen atom. In such a case, the compound (I) may be collected in a form of acid salts. Acids with which the compound (I) can form the acid salts may for example be inorganic acids (e.g. sulfuric acid, nitric acid, hydrochloric acid, hydrobromic acid, phosphoric acid and carbonic acid) and organic acids (e.g. acetic acid, propionic acid, palmitic acid, benzoic acid, salicylic acid, phenylbutyric acid, naphthoic acid, glycolic acid, succinic acid, nicotinic acid, tartaric acid, maleic acid, malic acid, citric acid, fumaric acid, methanesulfonic acid, p-toluenesulfonic acid, cyclohexanesulfonic acid, picric acid and lactic acid).

The compound (I) exhibits analgesic, anti-inflammatory, anti-pyretic and anti-rheumatic actions in mammals including man and is useful in treating inflammatory diseases, pains, fevers and rheumatism.

Among the compounds (I), those wherein X is a halogen and $R_1$ is hydrogen are more desirable from the pharmacological view-point.

The compound (I) can be administered orally or parenterally. The compound (I) can be administered as such or in conventional dosage forms such as tablets, powder, granules, capsules, suppositories, solution, suspensions and injections with suitable conventional additives or excipients. Dosage may be varied with symptoms of diseases to be treated, types of compound (I), hosts and is so on and usually selected from an amount of about 0.1 mg. to about 10 mg./kg. of body weight a day.

EXAMPLE 1

In 3 ml. of ethanol, 3.5 g. of methyl 6-chloro-5-cyclohexylindan-1-carboxylate and 3 g. of hydrazine hydrate are heated under reflux for 2 hours. After cooling, the precipitated crystals are collected by filtration and recrystallized from methanol-water. The procedure yields 6-chlore-5-cyclohexylindan-1-carbohydrazide, Melting point: 127.5 - 130.0° C.

Elemental analysis ($C_{16}H_{21}ClNO$): Calcd. C, 65.63; H, 7.23; N, 6.90. Found: C, 65.28; H, 7.55; N, 6.90.

EXAMPLE 2

In 35 ml. of benzene is dissolved 2.97 g. of 6-chloro-5-cyclohexylindan-1-carbonyl chloride and to the solution is added 1.77 g. of n-propylamine under cooling and with stirring. The mixture is stirred at room temperature for 1 hour, after which time it is washed with water and dried over anhydrous magnesium sulfate. The solvent is evaporated under reduced pressure and the residual crystals are recrystallized from acetone. The procedure yields N-propyl-6-chloro-5-cyclohexylindan-1-carboxamide, Melting poing: 140.5 – 142.5° C.

Elemental analysis ($C_{19}H_{26}ClNO$): Calcd. : C, 71.34; H, 8.19; N, 4.38. Found : C, 71.04; H, 8.46; N, 4.24.

The following compounds are synthesized by procedures similar to those described in Examples 1 and 2. The procedure used wherein the starting compounds are esters as in Example 1 and the procedure used wherein the materials are acid halides as in Example 2 will be referred to as "process A" and "process B", respectively.

Incidentally, the hydrochloride is obtained by the action of hydrochloric acid on the product in the usual way.

| X | $R_1$ | $R_2$ | Process | m.p. (° C) | Elemental analysis Calcd. Found C(%) | H(%) | N(%) |
|---|---|---|---|---|---|---|---|
| —Cl | —CH₃ | —CH₃ | B | 122.5–123.5 | 70.69 70.78 | 7.91 7.94 | 4.58 4.49 |
| —Cl | —H | —OH | B | 164.0–167.0 | 65.41 65.41 | 6.86 6.88 | 4.77 4.65 |
| —Cl | —H | —CH₂CH₂ | A | 122.0–123.5 | 75.47 75.61 | 7.39 7.52 | 3.67 3.54 |
| —Cl | —H |  | A | 188.5 –189.5 | 74.67 74.95 | 6.84 6.99 | 3.96 4.00 |
| —Cl | —H | 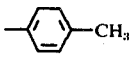—CH₃ | B | 200.0 –202.0 | 75.14 | 7.12 7.15 | 3.81 3.82 |
| —Cl | —H | 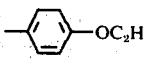—OC₂H₅ | A | 209.0–210.0 | 72.44 72.60 | 7.09 6.93 | 3.52 3.57 |
| —Cl | —H | 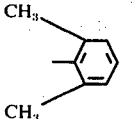 | B | 206.0–209.0 | 75.47 75.35 | 7.39 7.41 | 3.67 3.46 |

-continued

| X | R₁ | R₂ | Process | m.p. (°C) | C(%) | H(%) | N(%) |
|---|---|---|---|---|---|---|---|
| —Cl | —H | —⟨⟩—SO₂NH₂ | A | 246.5–249.0 | 61.03 / 61.24 | 5.82 / 5.70 | 6.47 / 6.41 |
| —H | —H | —⟨⟩—Cl | A | 195.0–197.0 | 74.67 / 74.85 | 6.84 / 6.70 | 3.96 / 3.82 |
| —Cl | —H | —CH₂CH₂N(CH₃)₂ | A | 142.0–144.0 | 68.85 / 68.63 | 8.38 / 8.51 | 8.03 / 8.27 |
| —Cl | —H | —CH₂CH₂OH | B | 125.5–126.5 | 67.17 / 67.32 | 7.52 / 7.60 | 4.35 / 4.37 |
| —Cl | CH₂—CH₂—OH | —CH₂CH₂OH | B | 131.0–132.0 | 65.65 / 65.45 | 7.71 / 7.77 | 3.83 / 3.72 |
| —Cl | H | CH₃ | B | 153.0–155.5 | 69.97 / 70.08 | 7.60 / 7.53 | 4.80 / 4.77 |
| —Cl | —H | —NH—⟨⟩ | B | 112.0–113.0 | 71.63 / 71.36 | 6.83 / 6.71 | 7.59 / 7.46 |
| —Cl | —H | —NH—⟨⟩—Cl | A | 163.0–164.0 | 65.51 / 65.03 | 6.00 / 5.90 | 6.95 / 6.90 |
| —Cl | —H | —N(CH₃)(CH₃) | B | 177.0–179.0 | 67.38 / 67.50 | 7.85 / 7.86 | 8.73 / 8.67 |
| —Cl | —⟨⟩ | —NH—⟨⟩ | A | 184.0–190.0 | 75.57 / 75.56 | 6.57 / 6.55 | 6.30 / 6.24 |
| —Cl | —CH₂CH₂CH₂CH₂CH₂— | | B | 177.5–179.5 | 72.92 / 72.99 | 8.16 / 8.02 | 4.05 / 4.03 |
| —Cl | —CH₂CH₂OCH₂CH₂— | | B | 146.0–154.0 | 69.05 / 69.22 | 7.53 / 7.50 | 4.03 / 4.06 |
| —Cl | —CH₂CH₂N(CH₃)CH₂— | | A | 260.5–261.5* | 63.47 / 62.92 | 7.61 / 7.50 | 7.05 / 6.88 |

Note:
*hydrochloride

We claim:
1. A compound of the formula

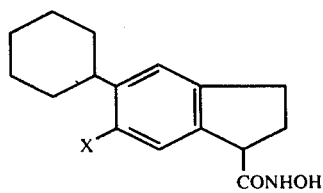

wherein X represents halogen.
2. The compound as claimed in claim 1, wherein X is chlorine.

* * * * *